United States Patent
Joshi et al.

(10) Patent No.: US 7,148,358 B2
(45) Date of Patent: Dec. 12, 2006

(54) PROCESS FOR THE PREPARATION OF S(−) AMLODIPINE-L(+)-HEMI TARATARTE

(75) Inventors: Rohini Ramesh Joshi, Pune (IN); Ramesh Anna Joshi, Pune (IN); M. K. Gurjar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/937,564

(22) Filed: Sep. 10, 2004

(65) Prior Publication Data
US 2005/0176781 A1   Aug. 11, 2005

(51) Int. Cl.
*C07D 213/803* (2006.01)

(52) U.S. Cl. ............................................ 546/321
(58) Field of Classification Search ................ 546/321
See application file for complete search history.

(56) References Cited

U.S. PATENT DOCUMENTS 6,046,338 A * 4/2000 Spargo ........................ 546/322
6,822,099 B1 * 11/2004 Senanayake et al. ........ 546/319

* cited by examiner

*Primary Examiner*—Patricia L. Morris
(74) *Attorney, Agent, or Firm*—Buchanan Ingersoll & Rooney, PC

(57) ABSTRACT

The present invention relates to a process for the preparation of [S(−) amlodipine-L(+)-hemi taratarte] from RS amlodipine base using L(+) tartaric acid in the presence of dimethyl sulfoxide.

6 Claims, No Drawings

PROCESS FOR THE PREPARATION OF S(−) AMLODIPINE-L(+)-HEMI TARATARTE

FIELD OF THE INVENTION

The present invention relates to a process for the preparation of [S(−) amlodipine-L(+)-hemi taratarte] from RS amlodipine base using L(+) tartaric acid in the presence of dimethyl sulfoxide.

BACKGROUND OF THE INVENTION

Amlodipine and its salts are long acting calcium channel blockers and are useful for the treatment of cardiovascular disorders. Racemic Amlodipine is currently being used as its besylate in the treatment of hypertension and angina. The preparation of racemic compound is described in European patent 0089167. Amlodipine is racemic compound and has chiral center at 4 position of the dihydropyridine ring.

It has also been reported that the R(+) isomer is a potent inhibitor of smooth muscle cell migration (PCT/EP-94/02697). The S(−) isomer is having calcium channel blocker activity while the R(+) isomers has little or no calcium channel blocking activity.

Prior art for the preparation of R and S enantiomers of amlodipine are a) resolution of amlodipine azide ester with optically active 2-methoxy-2-phenylethanol (J. Med. Chem., 29, 1696, 1986. J. E. Arrowsmith, S. F. Campbell, P. E. Cross, J. K Stabs, R. A., Burges and EP Appl. 0331315A) or b) resolution of Amlodipine base with optically active camphanic acid [J. Med. Chem., 35, 3341, 1992, S. Goldman, J. Stoltefuss and L. Born) or c) resolution of RS-amlodipine base to R(+) and S(−) isomer with L or D tartaric acid respectively in organic solvent DMSO {Peter L., Spargo U.S. Pat. No. 6,046,338; (2000), PCT 95/25722 (1995)] which indicate the use of both tartaric acids is essential.

The Disadvantages:

The main disadvantages of the prior art are:
1. The use of unnatural tartaric acid for the separation of S(−) amlodipine
2. The use of costlier camphanic acid or 2-methoxy-2-phenylethanol as a resolving agents.

OBJECTS OF THE INVENTION

The main object of the invention is to develop a technology for the preparation of S(−) amlodipine from racemic amlodipine using naturally occurring L-tataric acid.

SUMMARY OF THE INVENTION

Accordingly, the invention provides a new and efficient process for the preparation of [S(−) amlodipine-L(+)hemi tartarte] in good yield with high enantiomeric purity by reacting RS amlodipine base with L(+) tartaric acid in an organic solvent at a temperature ranging from 20–35° C. for a period ranging from 16 to 24 hours, separating by filtration solid [R(+) amlodipine-L(+)-hemi taratarte], seeding the filtrate to obtain solid [S(−) amlodipin-L(+)-hemi taratarte], filtering and recrystallising the solid, basifying to obtain S(−) amlodipine.

In one embodiment of the present invention the organic solvent used for the reaction is dimethyl sulfoxide.

In another embodiment of the present invention 0.5 mole of L(+) tartaric acid is used for the reaction.

In another embodiment the solvent used for crystallization is selected from the group consisting of methanol, ethanol and butanol.

In another embodiment of the invention basification is done using metal hydroxides, carbonates or aq. Ammonia

DETAILED DESCRIPTION OF THE INVENTION

The unique feature of the invention is preferential crystallization of enantiomer salt with respect to quantity of DMSO and time. The process of resolution of RS amlodipine using L(+) tartaric acid is shown in the scheme below:

SCHEME

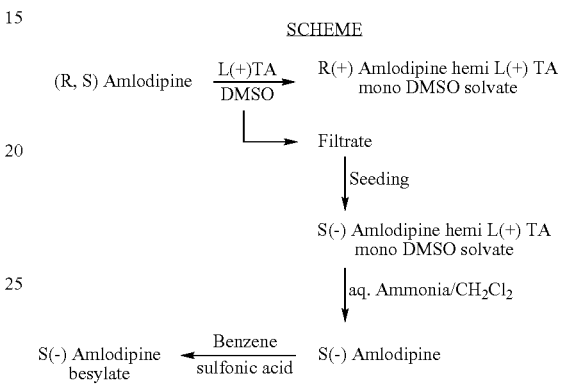

The process of the present invention is described herein below with reference to examples which are illustrative only and should not be construed to limit the scope of the present invention in any manner.

EXAMPLE-1

Amlodipine hemi L tartarate-mono-DMSO solvate mp 160–162° C. [α]$^t$=+24.32 (c=1, R(+) Amlodipine-hemi-L-tartarate mono DMSO solvate and S(−) Amlodipine-hemi-L tartarate mono DMSO solvate from (RS) Amlodipine To a stirred solution of 10.50 gm (0.0256 mole), of RS Amlodipine in 30 ml of DMSO was added a solution of 1.93 (0.128) mole (0.5 equiv) of L(+) Tartaric acid in 30 ml DMSO. The solid starts separating from clear solution within 5–10 min. This was stirred for 3 hrs. and the solid was filtered off, washed with acetone and dried to give 6.66 gm, 46.15% R(+) MeOH). The filtrate was seeded with S(−) amlodipine hemi L(+) tartarate salt. and left overnight the solid was filtered off and washed with 10 ml acetone and dried to give 6.41 gm, 44.4% S(−) amlodipine-hemi L(+)-tartarate mono DMSO solvate. mp 169.5–171.5° C.=−14.1 (c=1, MeOH) 90% de by chiral HPLC. (J. Chrom., B 693, 367 (1997) J. Luksa, Dj. Josic, B. Podobinc, B. Furlan, M. Kremser]

EXAMPLE-2

RS Amlodipine L(+) tartarate mono DMSO solvate from RS Amlodipine

The procedure as described in example 1 was repeated and the reaction was kept overnight. The solid filtered and dried to yield 14 gm, 97.9% RS Amlodipine L(+) tartarate mono DMSO solvate. Mp 148.5–151° C. (c=1 MeOH) 3.3% de by chiral HPLC.

EXAMPLE-3

S(−) Amlodipine hemi L(+) tartarate monohydrate from S(−) Amlodipine-hemi-L (+) tartarate monohydrate DMSO solvate-methanol as solvent.

50 gms of S(−) Amlodipine-hemi-L(+)-tartarate mohohydrate DMSO solvate was dissolved in 250 ml refluxing methanol (30 min). The solution was kept overnight at room temperature (25–28° C.) with stirring. The solid was collected by filtration, washed with 100 ml methanol and dried at 50° C. in vacuo (2 hrs till constant wt.) to give 35 gm (80%). S(−) Amlodipine-hemi-L(+)-tartarate monohydrate. Mp 171–172° C.=114.1 (c=1, MeOH); 90% de chiral HPLC.

EXAMPLE-4

S(−) Amlodipine hemi L(+)-tartarte mohohydrate from S(−) Amlodipine-hemi-L-(+) tartarate monohydrate DMSO solvate—Ethanol as solvent.

The procedure was followed as mentioned in example 3 was using ethanol (150 ml) instead of methanol. The solid obtained was collected by filtration, washed with 50 ml cold ethanol and dried at 50° C. in vacuo (2 hrs till constant wt.) to give 30 gms (68%). S(−) Amlodipine hemi L(+) tartarate monohydrate mp 172.5–174° C.=17.44 (C=1, MeOH), 97% de chiral HPLC.

EXAMPLE-5

S(−) Amlodipine from (S)(−) amlodipine hemi L (+) tartarte monohydrate.

S(−) Amlodipine hemi L(+) tartarate mohohydrate (30 gms) was slurried in 60 ml $CH_2Cl_2$ and 60 ml (6%) aqueous ammonia for 30 mm. The organic solution was separated and washed with water. The organic extract was dried to give solid. The solid was filtered and dried at room temperature under vacuo to give 20 gms (82%) S(−) amlodipine mp 108–109° C. 30.55 (c=1, MeOH), 97.4% ee by chiral HPLC.

EXAMPLE-6

S(−) Amlodipine from S(−) amlodipine hemi L(+) tartarte mono DMSO solvate

S(−) Amlodipine hemi L(+)-tartarate mono DMSO solvate (30 gms) was slurried in 60 ml $CH_2Cl_2$ and 60 ml (6%) aqueous ammonia for 30 min. The organic solution was separated and washed with water. The organic extract was dried over anhydrous sodium sulphate and concentrated. The residue was triturated with hexane to give solid 20.1 gms (92%) S(−) amlodipine. Mp 107–107.5° C. 27.3 (c=1, MeOH), 90% ee by chiral HPLC.

We claim:

1. A process for the preparation of [S(−) amlodipine-L(+)-hemi tartarate which comprises reacting RS amlodipine base with L(+) tartaric acid in an organic solvent at a temperature ranging from 20–35° C. for the period ranging from 16 to 24 hours, separating the solid [R(+) amlodipine-L(+)-hemi tartarate] by filtration, seeding the filtrate to obtain solid [S(−) amlodipine-L(+)-hemi tartarate] by precipitation, filtering the solid and basifying to obtain S(−) amlodipine.

2. The process claimed in claim 1 wherein the solvent is DMSO.

3. The process claimed in claim 1 wherein the solvent to amlodipine ratio is 5–6 ml/gm of amlodipine.

4. The process claimed in claim 1 wherein L-tartaric acid employed is about 0.5 mole per mole of amlodipine.

5. The process claimed in claim 1 wherein the solvate precipitated is S(−) amlodipine hemi L(+)-tartarate mono DMSO solvate.

6. The process claimed in claim 1 wherein a stirred solution of RS Amlodipine in DMSO was added to a solution of L(+) Tartaric acid in DMSO, the solid obtained separated by filtration, washed with acetone, dried to give R(+) MeOH), the filtrate seeded with S(−) amlodipine hemi L(+) tartarate salt, the solid so obtained filtered off and washed with acetone and dried to give S(−) amlodipine-hemi L(+)-tartarate mono DMSO solvate.

* * * * *